United States Patent [19]

Pepe et al.

[11] Patent Number: 5,218,133

[45] Date of Patent: Jun. 8, 1993

[54] PROCESS FOR MAKING A SILYLISOCYANURATE

[75] Inventors: Enrico J. Pepe, Amawalk; Shiu-Chin H. Su, Croton-on-Hudson, both of N.Y.; Scot M. Turner, Marietta, Ohio

[73] Assignee: Union Carbide Chemicals & Plastics Technology Corporation, Danbury, Conn.

[21] Appl. No.: 932,584

[22] Filed: Aug. 20, 1992

[51] Int. Cl.$^5$ .................................. C07F 7/10
[52] U.S. Cl. ........................... 556/420; 544/193
[58] Field of Search .................... 556/420; 544/193

[56] References Cited

U.S. PATENT DOCUMENTS

| | | | |
|---|---|---|---|
| 2,642,916 | 8/1953 | Kaiser | 544/183 X |
| 2,952,665 | 9/1960 | Berge et al. | 544/193 X |
| 3,511,866 | 5/1970 | Pepe | 260/448 |
| 3,517,001 | 6/1970 | Berger | 260/248 |
| 3,584,024 | 6/1971 | Pepe | 260/448 |
| 3,598,852 | 8/1971 | Berger | 260/248 |
| 3,607,901 | 9/1971 | Berger | 260/448 |
| 3,821,218 | 6/1974 | Berger | 260/248 |
| 4,124,545 | 11/1978 | Hocker | 544/193 X |
| 4,496,754 | 1/1985 | Kanner et al. | 556/420 |
| 4,631,346 | 12/1986 | Webb et al. | 556/420 |
| 4,831,173 | 5/1989 | Kriausy et al. | 556/420 |
| 4,880,927 | 11/1989 | Takago et al. | 544/193 |
| 5,075,260 | 12/1991 | Dell'amico et al. | 556/420 |

*Primary Examiner*—Paul F. Shaver
*Attorney, Agent, or Firm*—B. L. Deppenbrock

[57] ABSTRACT

This invention provides a process for making a silylorganocarbamate or a silylisocyanurate which process comprises reacting an aminosilane with a dialkyl carbonate, diaryl carbonate or a mixture thereof in the presence of a basic catalyst to obtain the silylorganocarbamate; optionally, neutralizing the basic catalyst and residual aminosilane with a neutralizing agent; and adding a cracking catalyst and heating at subatmospheric pressure to obtain the silylisocyanurate; or heating a silylorganocarbamate at a temperature sufficient for dissociation of the carbamate at subatmospheric pressure in the presence of a cracking catalyst and a timerization catalyst to obtain a silylisocyanurate.

20 Claims, No Drawings

PROCESS FOR MAKING A SILYLISOCYANURATE

BACKGROUND OF THE INVENTION

1. Field of the Invention

The present invention relates to processes for making a silylisocyanurate and a silylorganocarbamate. More particularly, the present invention relates to a process for making 1,3,5-tris[(trialkoxysilyl)alkyl] isocyanurates. The silylisocyanurate has utility as an accelerator or promoter for adhesion of room temperature vulcanizable organosiloxanes and silane modified polymers, as an additive for organosiloxane compositions suitable for fiber treatment and in automotive coatings. The silylorganocarbamate has utility as coupling agent for fiber glass and as agent for imparting water repellency.

2. Prior Art

U.S. Pat. No. 3,517,001 describes the hydrosilation of triallyl isocyanurate with various hydrosilanes added to the allyl groups in the presence of a catalyst such as platinum, rhodium, and the like. However, this process uses a large amount of catalyst because the isocyanuric acid ring acts as an inhibitor for the addition reaction. The addition reaction is incomplete due to the isomerization of the allyl group; and, thus, predominantly mono- and di- adducts are produced. The tri-adduct, i.e., the trisilylated isocyanurate product, is produced in low yield and is difficult to isolate.

U.S. Pat. No. 3,598,852 describes a process for making silylisocyanurate in which a haloorganosilane intermediate is reacted with a metal cyanate in the presence of a high boiling polar solvent such as dimethylformamide. Subsequently, the polar solvent is removed by vacuum stripping. However, the solvent is toxic and difficult to remove.

U.S. Pat. No. 4,880,927 describes a method for preparing silylisocyanurate in which the silylisocyanate is thermally treated or heated for cyclization to the trimer in the presence of a strongly basic catalyst such as alkali metal hydroxides or alkoxides. However, when this method is employed to prepare a silylorganoisocyanurate, it requires the isolation of toxic isocyanate and results in a highly colored product.

There is an on-going need to provide processes for preparing a silylisocyanurate, and a process for preparing a silylorganocarbamate, which processes are simple, produce the desired product in high yield, with little color and avoid the handling of toxic materials such as phosgene and isocyanate intermediates.

SUMMARY OF THE INVENTION

Accordingly, the above need can be met by the present invention which provides two processes for making a silylisocyanurate and a process for making a silylorganocarbamate.

There is provided a process for making a silylorganocarbamate which process comprises reacting an aminosilane with a dialkyl carbonate, diaryl carbonate or a mixture thereof in the presence of a basic catalyst, which process is hereinafter referred to as Process [A].

One process for making a silylisocyanurate comprises (1) reacting an aminosilane with a dialkyl carbonate, diaryl carbonate or mixture thereof in the presence of a basic catalyst; (2) neutralizing the basic catalyst and residual aminosilane with a neutralizing agent; and (3) adding a cracking catalyst and heating at subatmospheric pressure to obtain the silylisocyanurate, which process s hereinafter referred to as Process [B]. In Process [B] one or more of the following components: a cracking catalyst, a neutralization salt and a residual aminosilane serve as a trimerization catalyst. In a preferred embodiment of Process [B] a neutralizing agent is employed such that all the basicity of the basic catalyst is deactivated and at least 50% of the residual aminosilane reacts with the neutralization agent to minimize undesirable side reactions which can adversely affect the viscosity and purity of the desired final product.

Additionally, another process for making a silylisocyanurate comprises heating a silylorganocarbamate at a temperature sufficient for dissociation of the carbamate at subatmospheric pressure in the presence of a cracking catalyst and a trimerization catalyst, which process is hereinafter referred to as Process [C].

DETAILED DESCRIPTION OF THE PRESENT INVENTION

In the processes of the present invention the silylorganocarbamate and the silylisocyanurate are obtained in accordance with the following schematic chemical reaction equations:

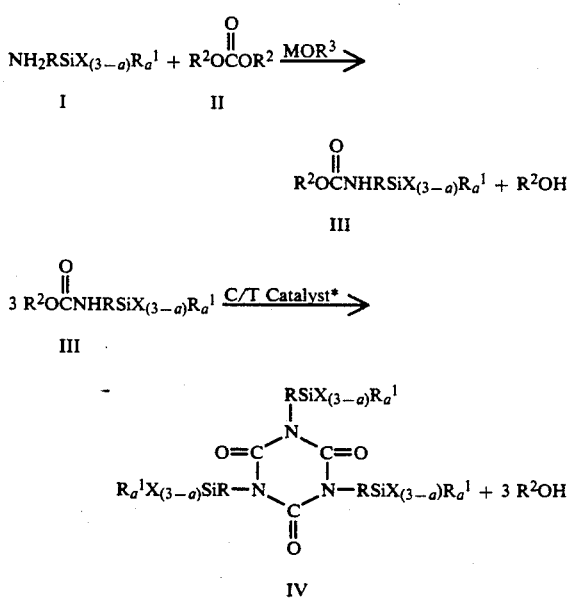

\* = Cracking and/or Trimerization Catalyst

In the above schematic chemical reaction equations, Formula III is a silylorganocarbamate and Formula IV is a silylisocyanurate. In both Formulae III and IV:

R is a divalent hydrocarbon group having 2 to 11 carbon atoms preferably 3 to 5 carbon atoms;

$R^1$ is selected from the group consisting of
  (i) an alkyl- or halogenated alkyl-group having 1 to 8 carbon atoms;
  (ii) an aryl group having at least 6 ring carbon atoms;
  (iii) an aralkyl group;

X is a hydrolyzable group selected from the group consisting of (i) an alkoxy group, (ii) a trialkylsiloxy group and (iii) an alkoxy-substituted alkoxy group; and a is an integer from 0 to 3 inclusive.

Additionally, in Formula III for the silylorganocarbamate, $R^2$ is a monovalent hydrocarbon group selected from the group consisting of (i) an alkyl having 1 to 8 carbon atoms and (ii) an aryl having 6 to 8 carbon atoms.

Preferably, in Formulae III and IV, X is a hydrolyzable group selected from the group consisting of (i) an alkoxy group having the formula $R^5O—$; (ii) a trialkylsiloxy group having the formula $—OSiR^5_3$; and (iii) an alkoxy-substituted alkoxy group having the formula $(—OR^5(OR^5)_n$; wherein each $R^5$ is the same or different, linear or branched, substituted or unsubstituted, and is a monovalent hydrocarbon having 1 to 8 carbon atoms; and n is an integer ranging from 1 to 3 inclusive.

In Process [A] an aminosilane (Formula I) is reacted with a dialkyl- and/or diaryl- carbonate (Formula II) in the presence of a strongly basic catalyst to form a reaction mixture containing a silylorganocarbamate (Formula III), an alcohol by-product and excess carbonate, if employed. The alcohol and excess carbonate, if present, can be removed from the mixture, if desired, by means well known to those skilled in the art. Such removal means can include, for example, stripping or distillation under reduced or ambient pressure. Depending on the purpose and end use, if necessary, the basic catalyst can be removed from the reaction system by neutralization as described herein.

In Process [B], an aminosilane (Formula I) is reacted with a dialkyl- and/or diaryl- carbonate (Formula II) in the presence of a strongly basic catalyst to form a silylorganocarbamate (Formula III). Subsequently, the basic catalyst and residual aminosilane, if any, is neutralized with a neutralizing agent to form a weak base or salt. After neutralization, a weakly basic cracking catalyst is preferrably added to the reaction mixture and heat is applied at subatmospheric pressure to obtain the silylisocyanurate (Formula IV). If desired, after neutralization, the neutralization salt can be removed by means well known to those skilled in the art. The alcohol by-product and excess carbonate, if employed, are removed prior to or after the addition of the cracking catalyst, (i.e., before cracking occurs). In this process, the cracking catalyst, neutralization salt, and/or residual aminosilane serve as the trimerization catalyst.

In Process [C] of the present invention a silylorganocarbamate (Formula III) is heated at a temperature sufficient for dissociation of the carbamate at subatmospheric pressure in the presence of a cracking catalyst and a weak base trimerization catalyst to produce the silylisocyanurate (Formula IV). By dissociation, also referred to as pyrolysis, is meant that one or more bonds of the silylorganocarbamate break such that a silylorganoisocyanate and an alcohol by-product form. In general, the silyorganocarbamate is cracked by heating it to reflux under reduced or subatmospheric pressure. During such cracking, the alcohol is separated and can be caught in a trap such as a dry ice trap. In the presence of a trimerization catalyst, the silylorganoisocyanate is believed to trimerize in-situ to form the silylisocyanurate. Accordingly, the silylorganoisocyanate has never been isolated. Suitable temperature range for dissociation to occur is from about 140° C. to 400° C. and pressure ranges from about 1 to 500 mm/Hg.

Aminosilane

The aminosilane that is employed in Processes [A] and [B] of this invention is described by Formula I:

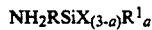

$NH_2RSiX_{(3-a)}R^1_a$ wherein R is a divalent hydrocarbon group having 2 to 11 carbon atoms, preferably having 3 to 5 carbon atoms;

$R^1$ is selected from the group consisting of
  (i) an alkyl- or halogenated alkyl- group having 1 to 8 carbon atoms, such as methyl, ethyl, propyl, isopropyl, butyl, hexyl, chloropropyl, and the like;
  (ii) an aryl group having at least 6 ring carbon atoms, such as phenyl, naphthyl, tolyl and the like;
  (iii) an aralkyl group, such as benzyl, phenylethyl, and the like;

X is a hydrolyzable group selected from the group consisting of (i) an alkoxy group ($R^5O—$), (ii) a trialkylsilyloxy group ($-OSiR^5_3$), and (iii) an alkoxy-substituted alkoxy group ($—OR^5(OR^5)_n$) wherein n is 1 to 3 inclusive; wherein each $R^5$ is the same or different, linear or branched, substituted or unsubstituted, and is a monovalent hydrocarbon having 1 to 8 carbon atoms; and a is an integer from 0 to 3 inclusive.

Illustrative of such aminosilanes are:
gamma-aminopropyltrimethoxysilane
gamma-aminopropyltriethoxysilane
gamma-aminopropylmethyldiethoxysilane
gamma-aminopropylmethyldimethoxysilane
gamma-aminopropylethyldiethoxysilane
gamma-aminopropylphenyldiethoxysilane
gamma-aminopropylphenyldimethoxysilane
delta-aminobutyltrimethoxysilane
delta-aminobutyltriethoxysilane
delta-aminobutylmethyldiethoxysilane
delta-aminobutylmethyldimethoxysilane
delta-aminobutylethyldiethoxysilane
delta-aminobutylethyldimethoxysilane
delta-aminobutylphenyldiethoxysilane
delta-aminobutylphenyldimethoxysilane
beta-aminoisopropyltrimethoxysilane
gamma-aminopropyltripropoxysilane
gamma-aminopropyltributoxysilane
gamma-aminopropylphenylmethyl-n-propoxy silane
gamma-aminopropylmethyldibutoxysilane
gamma-aminopropyl-tris(methoxyethoxyethoxy) silane
gamma-aminopropyldimethylethoxysilane
gamma-aminopropyldiethylmethylsilane
gamma-aminopropyl-tris(trimethylsiloxy)silane
ω-aminoundecyltrimethoxysilane
delta-aminobutyldimethylmethoxysilane
delta-amino(3-methylbutyl)methyldimethoxysilane
delta-amino(3-methylbutyl)methyldiethoxysilane
delta-amino(3-methylbutyl)trimethoxysilane Preferred aminosilanes are
gamma-aminopropyltrimethoxysilane;
gamma-aminopropyltriethoxysilane;
gamma-aminopropylmethyldimethoxysilane and
gamma-aminopropylmethyldiethoxysilane.

Aminosilanes useful in the Processes [A] and [B] of this invention are readily commercially available and their preparation is well known to those skilled in the art. In general, aminosilanes can be prepared by reacting an allylamine with an SiH-containing compound in the presence of a rhodium or ruthenium catalyst. Such preparations are disclosed, for example, in U.S. Pat. Nos. 4,888,436; 4,897,501; 4,921,988 and 4,927,953.

Organic Carbonate

In Processes [A] and [B] of the present invention an aminosilane of Formula I is reacted with a dialkyl carbonate, diarylcarbonate or a mixture thereof. Suitable carbonates for use as starting material in the Processes [A] and [B] of the present invention are described by Formula II:

$$R^2OCOR^2$$

wherein each $R^2$ is the same or different and is a monovalent hydrocarbon group selected from the group consisting of (i) an alkyl group having 1 to 8 carbon atoms, preferably an alkyl group having 1 to 4 carbon atoms and (ii) an aryl group having 6 to 8 carbon atoms.

Illustrative of such carbonates useful in the Processes [A] and [B] of the present invention are dimethyl carbonate; diethyl carbonate; dipropyl carbonate; dibutyl carbonate; diisobutyl carbonate; di-tert-butyl carbonate; di-isopentyl carbonate; di-isopropyl carbonate; ethylmethyl carbonate; ethyl-2-butoxyethyl carbonate; bis-(2-chloroethyl) carbonate; diphenyl carbonate; bis(o-m-chlorophenyl) carbonate; bis(o-p-chlorophenyl) carbonate; bis(dichlorophenyl) carbonate; bis(trichlorophenyl) carbonate; bis(o-,m-,p-tolyl) carbonate; and the like. Also included as suitable in the Processes [A] and [B] of the present invention are isomers and mixtures of such carbonates. Most preferred carbonates for use in the Processes [A] and [B] of the present invention are dimethyl carbonate; diethyl carbonate; and dipropyl carbonate. Additionally, dialkylcarbonates such as dialkylpyrocarbonates can be employed in Processes [A] and [B] of this invention. Illustrative dialkylpyrocarbonates can include, for example, dimethylpyrocarbonate, diethylpyrocarbonate, and di-t-butyl pyrocarbonate. However, while pyrocarbonates can be employed in Processes [A] and [B], they are generally not preferred because they are costly.

Carbonates employed in the Processes [A] and [B] of this invention are readily commercially available from a variety of suppliers such as Aldrich Chemical Company and PPG Industries, Inc..

The reaction of aminosilane and organic carbonate can be carried out using stoichiometric amounts of the reactants. However, preferably, an excess of the organic carbonate, from about 0.05 to 1 mole of organic carbonate per mole of aminosilane can be employed in the reaction. Most preferably, from about 0.1 to 0.4 moles of excess organic carbonate per mole of aminosilanes is employed.

Basic Catalyst

The reaction between the aminosilane and the organic carbonate of Processes [A] and [B] can take place in the absence of a basic catalyst. However, preferably the reaction is conducted in the presence of a strongly basic catalyst. The basic catalyst is an alkali metal alkoxide catalyst of the formula:

$$MOR^3$$

wherein $R^3$ is a monovalent hydrocarbon group having 1 to 5 carbon atoms selected from the group consisting of methyl, ethyl, propyl and butyl; and M is an alkali metal, such as, for example, lithium, sodium, potassium, cesium and the like. Preferably, M is sodium or potassium.

Illustrative examples of basic catalysts suitable for use in the Processes [A] and [B] of the present invention include sodium methoxide, sodium ethoxide, sodium propoxide, sodium tert-butoxide, potassium methoxide, potassium ethoxide, potassium propoxide potassium tert-butoxide and the like. Most preferably, sodium and potassium methoxides and ethoxides are used in the Processes [A] and [B] of the present invention. Such compounds are well-known and are readily commercially available such as, for example, from Aldrich Chemical Company.

The amount of basic catalyst employed in the Processes [A] and [B] of the present invention ranges from about 0.01 parts by weight to 2 parts by weight per 100 parts by weight of the aminosilane and organic carbonate employed in the reaction. Preferably, the amount of the basic catalyst ranges from about 0.2 to 0.6 parts by weight per 100 parts by weight of the aminosilane and organic carbonate.

The reaction of the aminosilane and organic carbonate is mildly exothermic. Typically, the aminosilane and organic carbonate are reacted in the presence of the basic catalyst such that the temperature of the reaction is maintained within a range of about 10° C. to 120° C., preferably 25° C. to 80° C., and most preferably from about 20° C. to 60° C. The temperature is maintained within these ranges by cooling using circulating cold water, an ice-bath, dry ice ($CO_2$) bath and/or controlling the rate of addition of one or both of the reactants or by other means known to those skilled in the art. If the reaction is conducted at higher temperatures, undesirable by-products, such as other amines and water can form. Generally, the reaction is conducted at ambient pressure under an atmosphere of a dry (no water) inert gas such as nitrogen or argon. This reaction can optionally be conducted at subatmospheric pressure to control reaction temperature.

Neutralizing Agent

In Processes [A] and [B] the aminosilane is substantially reacted with the organic carbonate to form a silylorganocarbamate (Formula III). Preferably, 97% to 99% of the aminosilane is reacted with the organic carbonate, as determined by gas chromatography or total base titration. The strongly basic catalyst and the unreacted aminosilane are neutralized by means of a neutralizing agent.

In Processes [A] and [B] suitable neutralizing agents can include inorganic acids such as anhydrous hydrochloric acid, anhydrous phosphoric acids and organic acids such as glacial acetic acid, propionic acid, butryic acid, hexanoic acid, oleic acid, maleic acid, fumaric acid, succinic acid, and the like. Most preferred acids for the processes of this invention are weak organic acids such as, for example, glacial acetic acid and anhydrous phosphoric acids, such as, for example, 105% phosphoric acid ("Superphosphoric Acid") and 115% phosphoric acid ("Polyphosphoric Acid") both of which are available from FMC Corporation (Philadelphia, Pa).

Preferably, in Process [B] this neutralization is accomplished such that all the basic catalyst reacts with the neutralizing agent to form a salt (i.e., a neutralization salt) and at least about 50% of the residual aminosilane reacts with the neutralizing agent. Preferably about 80% to 99% of the amine is neutralized. Most preferably 92% to 98% of the amine is neutralized. While an excess of neutralizing agent can be employed, an excess is generally not preferred because it can deactivate a cracking catalyst and/or a trimerization catalyst.

In Process [B] the amount of neutralizing agent ranges from about 0.65 to 0.995 equivalents of acid per equivalent of total base (derived from the basic catalyst and trace amount of unreacted, residual aminosilane). Preferably, the amount of neutralizing agent, or acid, ranges from about 0.85 to 0.995 equivalents of acid per equivalent of total base. Most preferably, the amount of neutralizing agent ranges from about 0.95 to 0.99 equivalents of acid per equivalent of total base.

In Process [B], optionally, after neutralization, the neutralization salt in the reaction mixture is removed by means well known to those skilled in the art. Commonly, such neutralization salt is removed by pressure or vacuum filtration without further cooling the reaction mixture using well known filtering aids such as, for example, a Celite ® and filtering paper. This filtration is typically conducted under a blanket of pressurized dry inert gas such as nitrogen or argon. Filtration is desirable at this point of the reaction for ease of handling. Filtration can also be conducted after the final product, a silylorganoisocyanurate, is formed.

In Process [B] the reaction mixture is stripped after neutralization and after filtration, if filtration is employed. Stripping can be performed after neutralizing but before the addition of the cracking catalyst and preferably is performed after the addition of the cracking catalyst. Stripping occurs at a reduced pressure of about 1 to 200 millimeter Hg (0.13 kPa to 26.7 kPa), and most preferably at a pressure of about 1 to 100 millimeter Hg (0.13 kPa to 13.3 kPa). The temperature at which stripping is performed ranges from about 60° C. to 160° C., and preferably ranges from about 120° C. to 150° C. such as vacuum stripping, is performed in order to remove excess organic carbonate, if any, and the alcohol by-product.

In Process [B] after completion of stripping and the addition of the cracking catalyst, the silylorganocarbamate (Formula III) is heated to a temperature ranging from about 160° C. to 250° C., preferably 190° C. to 210° C. under a reduced pressure which ranges from about 5 to 200 millimeters Hg (0.65 kPa to 26 kPa), preferably from about 15 to 75 millimeters Hg (2 kPa to 9.8 kPa) to form the silylisocyanurate.

Cracking Catalyst

In ProcesseB [B] and [C] the silylorganocarbamate (Formula III) is contacted with a cracking catalyst following neutralization. In Processes [B] and [C] the cracking catalyst is added to facilitate thermal dissociation of the silylorganocarbamate to alcohol and the silylorganoisocyanate which is believed to trimerize in-situ to form the silylisocyanurate. In this manner the cracking catalyst can serve as a trimerization catalyst in Processes [B] and [C] of the present invention. However, strongly basic cracking catalysts such as sodium methoxide are not preferred as cracking and trimerization catalysts due to a tendency to form colored and highly viscous products.

Compounds employed in the Processes [B] and [C] of the present invention as the cracking catalyst are generally well known and readily commercial available. Suitable for use as the cracking catalyst in the Processes [B] and [C] of the present invention are compounds having the formula:

wherein
  $M^1$ is selected from the group consisting of aluminum, titanium, magnesium and zirconium; and
  $R^4$ is the same or different and is a monovalent hydrocarbon group having 1 to 8 carbon atoms.
  X is an integer ranging from 2 to 4 inclusive.

Illustrative of such cracking catalysts are aluminum alkoxides, titanium alkoxides, magnesium alkoxides, and zirconium alkoxides. Suitable aluminum alkoxides for use in the Processes [B] and [C] of the present invention can include aluminum trimethoxide, aluminum triethoxide, aluminum triisopropoxide, aluminum tri-sec-butoxide, aluminum tri-tert-butoxide and the like.

Suitable titanium alkoxides for use in the Processes [B] and [C] of the present invention can include titanium (IV) methoxide, titanium (IV) ethoxide, titanium (IV) isopropoxide, titanium (IV) butoxide, titanium (IV) 2-ethylhexoxdde and the like.

In the Processes [B] and [C] of the present invention, suitable zirconium alkoxides can include zirconium (IV) ethoxide, zirconium (IV) propoxide, zirconium (IV) butoxide, zirconium (IV) isopropoxide, zirconium (IV) tert-butoxide, and the like.

Suitable magnesium alkoxides for use in Processes [B] and [] in the invention can include magnesium methoxide, magnesium ethoxide, magnesium butoxide, magnesium propoxide, and magnesium phenoxide.

Preferred cracking catalysts for use in the Processes [B] and [C] of the present invention are the aluminum alkoxides. A most preferred cracking catalyst is aluminum triethoxide.

Alternatively, a tin-containing compound can be used as a cracking catalyst in the Processes [B] and [C] of the present invention.

Illustrative of such tin-containing compounds can include organotin carboxylates such as, for example, dibutyltin dilaurate, dibutyltin diacetate, dibutyltin bis(2-ethylhexanoate). Other organotin compounds such as, for example, dibutyltin oxide, dibutyltin dimethoxide, dibutyltin dibromide, dibutyltin dichloride, di-tert-butyltin dichloride, dimethyltin dibromide, dimethytin dichloride, diphenyltin dichloride, and stannous octoate. Preferred among these tin-containing compounds are dibutyltin dilaurate, dibutyltin oxide, dibutyltin diacetate, and stannous octoate.

The amount of the cracking catalyst employed in the Processes [B] and [C] of the present invention can be readily determined by one skilled in the art. In general, the amount of cracking catalyst ranges from about 0.01% to 0.5% by weight, preferably from about 0.05% to 0.2% by weight based upon the total amount of the silylorganocarbamate.

Trimerization Catalyst

Catalysts for trimerization of aliphatic and aromatic isocyanates to form isocyanurates have been known for those skilled in the art and are disclosed, for example, by K. C. Frisch and L. P. Rumao in "/Catalysis in Isocyanate Reactions", *J. Macromol, Sci.-Revs. Macromol Chem.*, C5(1), 105-109 (1970). Illustrative compounds that can be employed in Processes [B] and [C] of the present invention as a trimerization catalyst include calcium acetate, potassium acetate, sodium carbonate, sodium methoxide, triethylamine, oxalic acid, sodium benzoate, soluble compounds of iron, potassium, magnesium, mercury, nickel, copper, zinc, chromium, aluminum, tin, vanadium, and titanium, triethyl phosphine, and titanium tetrabutyrate.

Compounds that can be employed in Processes [B] and [C] of the present invention as the trimerization catalyst are generally well known to one skilled in the art. Also suitable for use as the trimerization catalyst in the Processes [B] and [C] of the present invention are compounds included herein as the cracking catalyst and as the aminosilane. Additionally, an alkali metal salt of an organic acid, an alkali metal salt of phosphoric acid, and amines other than the aminosilanes described herein can be employed in the processes of the present invention as the trimerization catalyst.

Examples of alkali metal salts of organic acids can include the sodium, potassium, lithium, and cesium salts of glacial acetic acid, propionic acid, butyric acid, hexanoic acid, oleic acid, maleic acid, fumaric acid, succinic acid and the like. Examples of alkali metal salts of phosphoric acid can include trialkali metal orthophosphates such as trisodium orthophosphate, tripotassium orthophosphate, and dialkali metal orthophosphates such as disodium orthophosphate and dipotassium orthophosphate. Amines other than the aminosilanes described herein which are suitable for use as trimerization catalyst can include, for example, N,N-dimethyldodecylamine available from Akzo Chemical and 1,4-diazobicyclo [2.2.2.] octane available as Dabco ® from Aldrich Chemical.

The amount of trimerization catalyst employed in the Process [C] of the present invention is not critical and can be readily determined by one skilled in the art. In general, the amount of trimerization catalyst ranges from about 0.005% to 2.0% by weight, preferably from about 0.05% to 0.5% by weight based upon the silylorganocarbamate. In the Processes [B] and [C] of present invention, the dissociation product of carbamate, a silylorganoisocyanate, is trimerized in situ to form silylisocyanurate. In the Processes [B] and [C] of present invention, enough heat is provided for the cracking of the silylorganocarbamate in the presence of the cracking catalyst and enough vacuum is provided to remove the alcohol by-product while the pressure is high enough so that no silylorganoisocyanate is removed.

Other Considerations

Depending on the type and amount of neutralizing agent employed in the Process [B] of the present invention and the end-use of the final product, the pH of the silylisocyanurate is adjusted, if necessary, such that it ranges from about 5.5 to 8.5. Adjusting the pH of the silylisocyanurate to be within this range decreases the tendency of the silylisocyanurate to hydrolyze by contact with moisture and results in a more stable, easier to handle product.

Optionally, after the pH adjustment, if employed, the silylisocyanurate is filtered as described herein to remove any foreign particles and/or neutralization salt. The silylisocyanurate produced by the Process [B] of the present invention is usually a viscous liquid but can be a solid depending on the particular aminosilane used. Depending on how effectively oxygen is excluded or eliminated from the reaction process throughout, the silylisocyanurate so produced can range in color from light amber (less than 1 GVS) to dark brown (approximately 8 GVS).

The following examples are set forth for illustrative purposes only and are not to be construed as unduly limiting of the present invention. All parts and percentages are by weight unless otherwise specified.

EXAMPLES

EXAMPLE 1. PREPARATION OF 1,3,5-TRIS[3-(TRIMETHOXYSILYL)PROPYL] ISOCYANURATE

Preparation of intermediate methyl N-3-(trimethoxysilyl)-propylcarbamate (Step 1)

3-aminopropyltrimethoxysilane (179.3 grams, 1.0 moles) was charged to a 250 ml. dropping funnel attached to a 500 ml. 3-necked round bottom Pyrex ® flask equipped with mechanical stirring assembly, thermometer and a cold water bath. A one foot long, ⅜ inch diameter Vigreaux ® column outfitted for conventional vacuum distillation was also attached.

Under a dry-nitrogen atmosphere, dimethylcarbonate (108.1 grams, 1.2 moles), 99% grade from Aldrich Chemical Co., and sodium methoxide (0.86 grams, 0.016 moles as 3.5 grams of 25 wt % sodium methoxide solution in methanol from Aldrich Chemical Co.) were added to the flask. Over a 30 minute period, all of the 3-aminopropyltrimethoxysilane (Union Carbide A-1110) was added at a rate such that the reaction temperature was maintained in the range of 25°±5° C. throughout the addition. After an additional 3 hours at ambient temperature, the reaction mixture was heated by an electric heating mantle to 50°±5° C. for about 1 hour to complete the reaction. Titration of an aliquot sample with aqueous hydrochloric acid, in methanol solvent and bromocresol green indicator (approx. 1-2 drops) showed 0.13 moles/kilogram of total base.

Analysis by $^{13}C$, $^1H$, $^{29}Si$ NMR, Infrared spectral survey and gas chromatography connected to a mass spectrometer operating in the electron beam ionizing mode (EI) confirmed a high purity yield of methyl N-3-(trimethoxsilyl)propylcarbamate, $CH_3O-CONH(CH_2)_3Si(OCH_3)_3$ with about 2% of residual aminosilane.

Neutralization of sodium methoxide, residual amine and conversion of carbamate intermediate to isocyanurate (Step 2)

The methyl N-trimethoxysilylpropylcarbamate (237 grams, 1.0 moles) produced in Step 1 along with the excess dimethylcarbonate used in Step 1 and the methanol produced as by-product in Step 1 were subsequently treated with glacial acetic acid (2.19 grams, 0.0365 equivalents) equivalent to 98% of total residual base. Aluminum triethoxide (0.29 grams, 0.1 weight percent, from Aldrich Chemical Co.) was added. The stirred reaction mixture was then heated to about 150° C. at 20 mm mercury pressure to remove the stoichiometric amount of by-product methanol and excess dimethylcarbonate to a dry-ice trap. A clean trap was installed and commencing at about 160° C./20 mm. mercury pressure, continuous evolution and collection of stoichiometric methanol in the dry-ice trap was observed. A cold water condenser in the distillation setup maintained a total reflux condition and minimized carryover of carbamate intermediate to the receiver. Over a three hour period, the reactor temperature rose to 200° C. and was held for an additional 2 hours. Upon cooling, Celite ® 521 filter aid (2.9 grams, 1 weight percent, Aldrich Chemical Co.) was added and the reaction mixture pressure filtered using dry nitrogen. The clear, light amber (GVS-1), liquid filtrate (having a viscosity of 421 centistokes at 25° C.) was analyzed by $^{13}C$, $^1H$, $^{29}Si$ NMR and gas chromatography interfaced to a mass spectrometer operating in the electron beam ionizing mode (EI).

The product was compared to and found to be identical to a high purity sample of 1,3,5-tris[3-(trimethoxysilyl)propyl] isocyanurate,

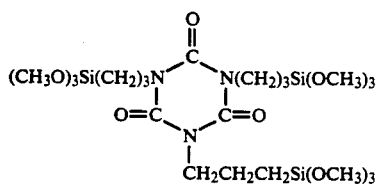

produced by trimerization of a purified sample of 3-isocyanatopropyltrimethoxysilane with a catalytic amount of the strong base sodium methoxide, (i.e., in accordance with the procedure of U.S. Pat. No. 4,880,927).

EXAMPLE 2. PREPARATION OF 1,3,5-TRIS[3-METHYLDIMETHOXYSILYL)PROPYL] ISOCYANURATE

The procedure of Example 1 is repeated with 163.3 grams, 1.0 moles of 3-aminopropylmethyldimethoxysilane substituted as the starting aminoorganosilane. The reaction mixture is subsequently treated with 98 mole % of the total residual base (0.10 moles/kilogram). Thus, 1.6 grams, 0.0266 moles of glacial acetic acid and 0.27 gram of aluminum triethoxide are added sequentially and the silylorganocarbamate processed over a four hour period at 200° C. to produce a 1,3,5-tris[3-(methyldimethoxysilyl)Propyl]-isocyanurate.

EXAMPLE 3. PREPARATION OF 1,3,5-TRIS[3-(TRIMETHOXYSILYL)PROPYL] ISOCYANURATE

3-Aminopropyltrimethoxysilane (463 pounds) and 8.36 pounds of sodium methoxide (26.6 wt. % in methanol) were charged to a 100 gallon reactor. Dimethylcarbonate was pumped to an auxillary tank. The system was deoxygenated by maintaining pressure at 50 mm Hg for 5 minutes, then breaking the vacuum with nitrogen. This procedure of deoxygenating was repeated twice.

Dimethylcarbonate was fed at a rate of about 6 gal./hr. while providing full cooling to the reactor jacket to assure the temperature remained less than 45° C. After 4.5 hours, the addition of dimethylcarbonate was completed. The reactor was heated to 50° C. and held at that temperature for 2.5 hours. The total base analysis (titration with HCl with Bromocresol green indicator) showed 0.15 wt. % NH2, [(mlHCl)×(Normality of HCl)×1.6/(weight of sample)], or 0.094 milli-equivalent base/gram sample.

Sodium methoxide and residual aminosilane were neutralized by glacial acetic acid (1800 ml.). Two scoops of Celite 545 were added to the reactor. The reaction product was recycled through a pressure filter to afford a clean and clear product, methyl N-3(trimethoxysilyl) propylcarbamate.

Following the filtration, aluminum triethoxide (340 g., Aldrich) was charged to the reactor. The system was deoxygenated as before and the system adjusted to approximately 50 mm Hg. The reactor was heated to 100° C. and held at that temperature until the methanol and the excess dimethylcarbonate had been removed. The reactor was then gradually heated to 200° C. for 3 hours. Unreacted carbamate was found to be 2.2 wt. % by Gas Chromatography (GC) analysis. The reactor contents were cooled and the system adusted to atmospheric pressure with nitrogen. Glacial acetic acid (50 ml.) was then charged to the reactor. A final pressure filtration was accomplished prior to transferring the product to containers

EXAMPLE 4. PREPARATION OF 1,3,5-TRIS[3-(TRIMETHOXYSILYL)PROPYL] ISOCYANURATE

3-Aminopropyltrimethoxysilane (463 pounds) and 8.36 pounds of sodium methoxide (26.6 wt. % in methanol) were charged to a 100 gallon reactor. The system was deoxygenated by maintaining a pressure of 50 mm Hg for 5 minutes, then breaking the vacuum with nitrogen. This deoxygenating procedure repeated twice.

Dimethylcarbonate was fed at a rate of approximately 6 gal./hr. while providing cooling to the jacket to assure the temperature remained 40° C. or less. After 3 hours, the temperature was dropped to 35° C. Four hours later, the addition of dimethylcarbonate was completed and the reactor was heated to 50° C. and held for 4 hours. The total base analysis (titration with HCl and Bromocresol green indicator) showed 0.26 wt. % NH2, [(mlHCl)×(Normality of HCl)×1.6/(weight of sample)], or 0.15 milli-equivalents base/gram of sample.

Sodium methoxide and residual aminosilane were neutralized by glacial acetic acid (2930 ml.). Two scoops of Celite 545 were added to the reactor. The reaction product was recycled through a pressure filter to afford a clean, clear product.

Following the filtration, aluminum triethoxide (336 g., Aldrich Chemical) was charged to the reactor. The system was deoxygenated as before and the system adjusted to approximately 50 mmHg. The reactor was heated to 100° C. and held until the methanol and the excess dimethylcarbonate had been removed. The reactor was heated to 190"C. and held at 190° C. for 1 hour, then at 195° C. for 1+ hour and finally at 200° C. for about 1 hour. Unreacted carbamate was found to be 4.2 wt. % by Gas Chromatography (GC) analysis. The system was cooled and the vacuum broken with nitrogen. Glacial acetic acid (1120 ml.) was then charged to the reactor. A final filtration was accomplished by charging 2 scoops of Celite 545 to the reactor, and recycling through a 14-inch pre-coated Sparkler filter until clear. The product was filtered to a 55-gallon drum.

EXAMPLE 5. PREPARATION OF 1,3,5-TRIS[3-(TRIETHOXYSILYL)PROPYL] ISOCYANURATE

The procedure of Example 1 is repeated with 221.4 grams, 1.0 moles, of 3-aminopropyltriethoxysilane (Union Carbide A-1100), 141.6 grams, 1.2 moles, diethyl carbonate and 2.2 grams of sodium ethoxide (0.6 weight %). The total residual base (0.14 moles/kg is treated with 2.93 grams (0.0488 equivalents, 96% of total residual base) of glacial acetic acid. Aluminum triethoxide, 0.36 grams, is then added. The silylorganocarbamate is processed over a three hour period at 200° C. to produce 1,3,5-tris[3-(triethoxysilyl)propyl] isocyanurate.

EXAMPLE 6. PREPARATION OF 1,3,5-TRIS[3-(TRIETHOXYSILYL)PROPYL] ISOCYANURATE

The procedure of Example 5 is repeated, except that 3-aminopropyltriethoxysilane (Union Carbide A-1100) and diethyl carbonate is reacted at 60° C. The total base (0.15 moles/kg) is neutralized with 2.44 grams (0.052 equivalents) of 105% phosphoric acid (Superphosphoric acid from FMC Corporation) to produce 1,3,5-tris[3-(triethoxysilyl)propyl] isocyanurate.

EXAMPLE 7. PREPARATION OF 1,3,5-TRIS[3-(TRIETHOXYSILYL)PROPYL] ISOCYANURATE

The procedure of Example 6 is repeated, except that the total base (0.15 moles/kg) is neutralized with 2.86 grams (0.053 equivalents) of 115% phosphoric acid (Polyphosphoric acid from FMC Corporation) to produce 1,3,5-tris[3-(triethoxysilyl)propyl] isocyanurate.

EXAMPLE 8. PREPARATION OF 1,3,5-TRIS[3-(DIMETHYLMETHOXYSILYL)PROPYL] ISOCYANURATE

The procedure of Example 1 is repeated with 147.3 grams, 1.0 moles, of 3-aminopropyldimethylmethoxysilane substituted as the starting aminoorganosilane to produce 1,3,5-tris[3-(dimethylmethoxysilyl)propyl] isocyanurate.

EXAMPLE 9. PREPARATION OF ISOCYANURATE TRIMER FROM THE CRACKING/TRIMERIZATION OF CARBAMATOPROPYLTRIMETHOXYSILANE UTILIZING ALUMINUM TRIETHOXIDE AS CRACKING CATALYST AND POTASSIUM ACETATE AS TRIMERIZATION CATALYST.

A three necked round bottom Pyrex ® flask, equipped with magnetic agitator, thermometer, distillation head and nitrogen blanketing, was charged with 241.6 grams of carbamatopropyltrimethoxysilane, 0.27 grams of aluminum triethoxide (Aldrich), and 0.50 grams of potassium acetate (MCB Manufacturing). The mixture was heated from room temperature to 200° C. throughtout a period of 2 hours with stirring at ~40 mm Hg' vacuum. The system was held at 200° C. for an additional 5 hours, then cooled, and sampled for analysis. Gas chromatographic analysis revaled 83.3 wt. % of the isocyanurate (trimer).

EXAMPLE 10

Example 9 was repeated but with a charge of 244.4 grams of carbamatopropyltrimethoxysilane, 0.27 grams of aluminum triethoxide, and 0.52 grams of potassium acetate. The mixture was heated to 165° C. throughout a 30 minute period and held for one hour with stirring at ~40 m Hg vacuum. The system was then cooled and sampled for analysis. The procedure was then repeated (1 hour at 165° C., ~40 mm Hg, cool and sample for analysis.) Following this, the system was heated to 180° C., at ~40 mm Hg. Samples were taken after 30 minutes, 1½ hours and 2 hours. (Cooling down and heating up were repeated for each sample.)

Gas chromatographic analysis revealed the following:

| Sample Number | Temperature | Time at Temp. | wt. % of the isocyanurate |
| --- | --- | --- | --- |
| 1 | 165° C. | 1 hour | 25.3 |
| 2 | 165° C. | 2 hours | 37.4 |
| 3 | 180° C. | ½ hour | 64.8 |
| 4 | 180° C. | 1½ hour | 62.1 |
| 5 | 180° C. | 2 hours | 71.6 |

What is claimed is:

1. A process for preparing a silyl organocarbamate, which process comprises reacting an aminosilane with a dialkyl carbonate or, diaryl carbonate or a mixture thereof in the presence of a basic catalyst to form a reaction mixture containing the silylorganocarbamate.

2. The process of claim 1 wherein the aminosilane has the formula:

$$NH_2RSiX_{(3-a)}R^1_a$$

wherein
R is a divalent hydrocarbon group having 2 to 11 carbon atoms;
$R^1$ is selected from the group consisting of
(i) an alkyl- or halogenated alkyl-group having 1 to 8 carbon atoms;
(ii) an aryl group having at least 6 ring carbon atoms;
(iii) an aralkyl group;
X is a hydrolyzable group selected from the group consisting of (i) an alkoxy group, (ii) a trialkylsilyloxy group, and (iii) an alkoxy-substituted alkoxy group, and
a is an integer from 0 to 3 inclusive.

3. The process of claim 1 wherein the dialkyl carbonate and diaryl carbonate have the formula:

$$R^2OCOR^2_{\phantom{2}}^{\phantom{2}} \text{ with } C=O$$

wherein each $R^2$ is the same or different and is a monovalent hydrocarbon group selected from the group consisting of (i) an alkyl group having 1 to 8 carbon atoms and (ii) an aryl group having 6 to 8 carbon atoms.

4. The process of claim 1 wherein the basic catalyst has the formula: $MOR^3$ wherein $R^3$ is a monovalent hydrocarbon group having 1 to 5 carbon atoms and M is an alkali metal.

5. The process of claim 1 wherein the reaction mixture is neutralized with a neutralizing agent.

6. The process of claim 1 wherein the silylorganocarbamate is separated from the reaction mixture by removing an alcohol by-product and excess carbonate from the reaction mixture.

7. The process of claim 1 wherein the silylorganocarbamate has the formula:

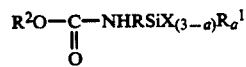

wherein
R is a divalent hydrocarbon group having 2 to 11 carbon atoms;
$R^1$ is selected from the group consisting of monovalent hydrocarbon group and a halogenated monovalent hydrocarbon group;

X is a hydrolyzable group selected from the group consisting
(i) an alkoxy group
(ii) a trialkysilyloxy group, and
(iii) an alkoxy-substituted alkoxy group;
a is an integer ranging from 0 to 3 inclusive; and
$R^2$ is an alkyl group having 1 to 8 carbon atoms.

8. A process for preparing an silylisocyanurate which process comprises:
   (1) reacting an aminosilane with a dialkyl carbonate or, diaryl carbonate or a mixture thereof in the presence of a basic catalyst to form a reaction mixture;
   (2) neutralizing the basic catalyst with a neutralizing agent;
   (3) adding a cracking catalyst while heating to obtain the silylisocyanurate.

9. The process of claim 8 wherein the aminosilane has the formula:

$$NH_2RSiX_{(3-a)}R^1_a$$

wherein
R is a divalent hydrocarbon group having 2 to 11 carbon atoms;
$R^1$ is selected from the group consisting of
(i) an alkyl- or halogenated alkyl-group having 1 to 8 carbon atoms;
(ii) an aryl group having at least 6 ring carbon atoms;
(iii) an aralkyl group;
X is a hydrolyzable group selected from the group consisting of
(i) an alkoxy group,
(ii) a trialkylsilyloxy group, and
(iii) an alkoxy-substituted alkoxy group; and
a is an integer from 0 to 3 inclusive.

10. The process of claim 8 wherein the dialkyl carbonate and diaryl carbonate have the formula:

$$R^2OCOR^2$$
$$\parallel$$
$$O$$

ps wherein each $R^2$ is the same or different and is a monovalent hydrocarbon group selected from the group consisting of (i) an alkyl having 1 to 8 carbon atoms and (ii) an aryl having 6 to 8 carbon atoms.

11. The process of claim 8 wherein the basic catalyst has the formula: $MOR^3$ wherein $R^3$ is a monovalent hydrocarbon group having 1 to 5 carbon atoms and M is an alkali metal.

12. The process of claim 8 wherein the cracking catalyst is selected from the group consisting of (i) a catalyst having the formula:

$$M^1(OR^4)_x$$

wherein
$M^1$ is selected from the group consisting of aluminum, titanium, magnesium and zirconium; each $R^4$ is the same or different and is a monovalent hydrocarbon group having 1 to 8 carbon atoms, and x is an integer ranging from 2 to 4 inclusive and (ii) a tin-containing compound.

13. The process of claim 8 wherein the reaction mixture is vacuum stripped after the neutralization step (2) and before the addition step (3).

14. The process of claim 8 wherein the reaction mixture is filtered after the neutralization step (2).

15. The process of claim 8 wherein the process is conducted under an atmosphere of a dr inert gas.

16. The process of claim 8 wherein the reaction mixture is vacuum stripped after the addition of step (3).

17. The process according to claim 8 wherein the neutralizing agent is employed such that all the basicity of the basic catalyst is deactivated and at least 50% of a residual aminosilane reacts with the neutralizing agent.

18. A process for preparing a silylisocyanurate, which process comprises: heating a silylorganocarbamate at a temperature sufficient for dissociation of the carbamate in the presence of (i) a cracking catalyst and (ii) a trimerization catalyst at subatmospheric pressure.

19. The process of claim 18 wherein the temperature ranges from 140° to 400° C. and the pressure ranges from 1 to 500 mm/Hg.

20. The process of claim 18 wherein the cracking catalyst has the formula:

$$M^1(OR^4)_x$$

wherein
$M^1$ is selected from the group consisting of aluminum, titanium, magnesium and zirconium; and each $R^4$ is the same or different and is a monovalent hydrocarbon group having 1 to 8 carbon atoms;
x is an integer ranging from 2 to 4 inclusive;
and the trimerization catalyst is selected from the group consisting of an amine, a salt of a weak organic acid, a salt of phosphoric acid and a mixture thereof.

* * * * *